United States Patent

Asaka et al.

Patent Number: 6,165,986
Date of Patent: Dec. 26, 2000

[54] ERYTHROMYCIN A DERIVATIVES

[75] Inventors: Toshifumi Asaka, Konosu; Masato Kashimura, Omiya; Akiko Matsuura, Tokorozawa; Tomohiro Sugimoto, Omiya; Tetsuya Tanikawa, Tokyo; Takaaki Ishii, Saitama, all of Japan

[73] Assignee: Taisho Pharmaceutical Co., Ltd., Japan

[21] Appl. No.: 09/355,827

[22] PCT Filed: Oct. 14, 1997

[86] PCT No.: PCT/JP97/03685

§ 371 Date: Aug. 5, 1999

§ 102(e) Date: Aug. 5, 1999

[87] PCT Pub. No.: WO98/40392

PCT Pub. Date: Sep. 17, 1998

[30] Foreign Application Priority Data

Mar. 10, 1997 [JP] Japan ................................. 9-055003

[51] Int. Cl.$^7$ .................................................. A61K 31/70
[52] U.S. Cl. .............................................. 514/29; 536/7.4
[58] Field of Search .................... 536/7.2, 7.4; 514/29

[56] References Cited

U.S. PATENT DOCUMENTS

| | | | |
|---|---|---|---|
| 4,331,803 | 5/1982 | Watanabe et al. | 536/7.2 |
| 4,742,049 | 5/1988 | Baker et al. | 514/29 |
| 5,444,051 | 8/1995 | Agouridas et al. | 514/29 |
| 5,561,118 | 10/1996 | Agouridas et al. | 514/29 |
| 5,656,607 | 8/1997 | Agouridas et al. | 514/29 |
| 5,770,579 | 6/1998 | Agouridas et al. | 514/29 |

FOREIGN PATENT DOCUMENTS 638584 4/1993 WIPO .
676409 4/1995 WIPO .

Primary Examiner—Elli Peselev
Attorney, Agent, or Firm—Lorusso & Loud

[57] ABSTRACT

An erythromycin A derivative represented by Formula (I):

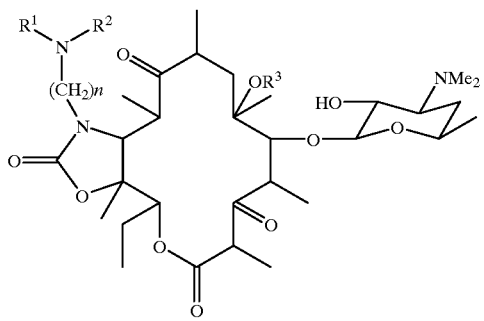

(wherein n is an integer of 2 to 4, $R^1$ is a pyridylmethyl group, a furylmethyl group, a thienylmethyl group, a quinolylmethyl group or a benzyl group having 1 to 3 substitutents selected from the group consisting of an alkyl group having 1 to 5 carbon atoms, a nitro group, an alkoxy group having 1 to 5 carbon atoms, an amino group and an amino group substituted by 1 or 2 alkyl groups having 1 to 5 carbon atoms, $R^2$ is the same group as defined for $R^1$, a hydrogen atom, an alkyl group having 1 to 5 carbon atoms, an acetyl group or a pyridylacetyl group, and $R^3$ is an alkyl group having 1 to 5 carbon atoms or a cinnamyl group) or a pharmaceutically acceptable salt thereof has a strong antibacterial activity against not only known erythromycin-sensitive bacteria but also erythromycin-resistant bacteria and Haemophilus influenzae.

2 Claims, No Drawings

ERYTHROMYCIN A DERIVATIVES

TECHNICAL FIELD

The present invention relates to antibiotic erythromycin A derivatives.

BACKGROUND ART

Erythromycin A is an antibiotic clinically widely used as an agent for treating infectious diseases caused by Gram-positive bacteria, mycoplasmas, etc. However, erythromycin A is decomposed by the gastric acid due to instability to acids, and thereby has a drawback of no constancy of movement in the body. Hitherto many erythromycin A derivatives have been prepared for the purpose of the improvement of the biological or pharmacological properties. For example, it is reported that 6-O-methylerythromycin A derivatives have an improved stability to acids and have a superior in vivo antibacterial activity in comparison with erythromycin A when administered orally (U.S. Pat. No. 4,331,803). Recently, it is also reported that 11,12-cyclic carbamate derivatives are prepared with the aim of expansion of antibacterial spectrum as well as stability to acids (EP. patent. No. 487411, U.S. Pat. No. 4,742,049, EP. Patent No. 676409 and ibid. 638584).

An object of the present invention is to provide a novel antibiotic erythromycin A derivative or a salt thereof having a strong antibacterial activity against not only known erythromycin-sensitive bacteria but also Haemophilus influenzae and erythromycin-resistant bacteria which recently are showing a tendency to increase, and a composition comprising the same as an effective component. Other objects of the present invention are to provide a method for the treatment of a bacterially infectious disease which comprises administering a pharmaceutically effective amount of the above-mentioned erythromycin A derivative or salt thereof to a patient, and use of the above-mentioned erythromycin A derivative or salt thereof for the treatment of a bacterially infectious disease.

The present inventors have variously researched on erythromycin A derivatives, in particular, their 11,12-cyclic carbamate compounds which have a certain substituted amino group on the nitrogen atom of the carbamate group at the 11-position, a methoxy group at the 6-position and a carbonyl group at the 3-position. As a result, compounds having the benzyl group substituted by an alkyl group, an alkoxy group (particularly, a methoxy group) or an amino group on the benzene ring have been found to have a stronger antibacterial activity against erythromycin-resistant bacteria than the compounds of which substituent on the nitrogen atom forming the carbamate group at the 11-position is a 2-(N-benzyl-N-methylamino)ethyl group (EP Patent No. 487411), and compounds having a pyridylmethyl group or a quinolylmethyl group other than the benzyl group have also been found to similarly have a strong activity. The present invention has been accomplished on the basis of the finds.

The present invention relates to an erythromycin A derivative represented by Formula (I):

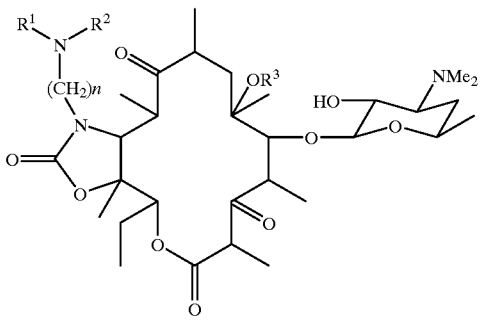

(wherein n is an integer of 2 to 4, $R^1$ is a pyridylmethyl group, a furylmethyl group, a thienylmethyl group, a quinolylmethyl group or a benzyl group having 1 to 3 substituents selected from the group consisting of an alkyl group having 1 to 5 carbon atoms, a nitro group, an alkoxy group having 1 to 5 carbon atoms, an amino group and an amino group substituted by 1 or 2 alkyl groups having 1 to 5 carbon atoms, $R^2$ is the same group as defined for $R^1$, a hydrogen atom, an alkyl group having 1 to 5 carbon atoms, an acetyl group or a pyridylacetyl group, and $R^3$ is an alkyl group having 1 to 5 carbon atoms or a cinnamyl group) or a pharmaceutically acceptable salt thereof.

In the above-mentioned formula, n is preferably 2 or 3. The alkyl group having 1 to 5 carbon atoms in the definition for $R^1$ refers to a straight or branched alkyl group, and is preferably a methyl group. The alkoxy group having 1 to 5 carbon atoms refers to a straight or branched alkoxy group, and is preferably a methoxy group, and the amino group substituted by 1 or 2 alkyl groups having 1 to 5 carbon atoms is preferably a dimethylamino group. The alkyl group having 1 to 5 carbon atoms in the definition for $R^2$ refers to a straight or branched alkyl group, and is preferably a methyl group, an ethyl group or a propyl group. The alkyl group having 1 to 5 carbon atoms in the definition for $R^3$ refers to a straight or branched alkyl group, and is preferably a methyl group.

The pharmaceutically acceptable salt refers to a salt used in chemotherapy or prophylaxis of bacterially infectious diseases, for example, a salt with acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, p-toluenesulfonic acid, laurylsulfuric acid, malic acid, aspartic acid, glutaminic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, polyacrylate or carboxyvinyl polymer.

The compounds of the present invention can be prepared, for example, as follows.

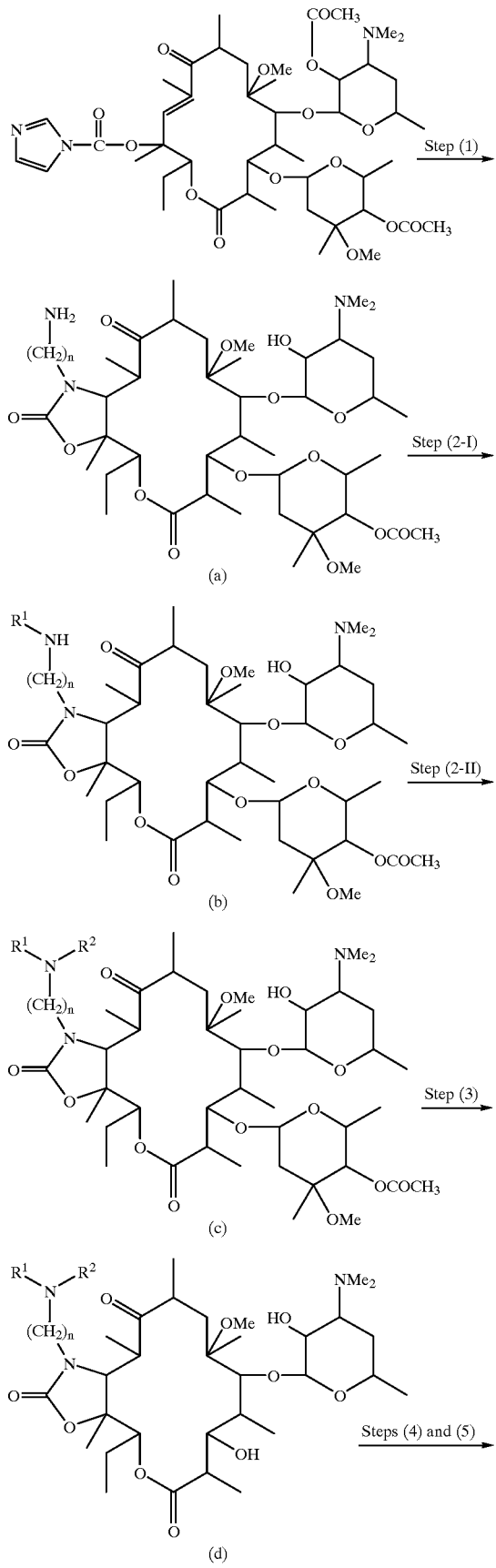

(a)
(b)
(c)
(d)

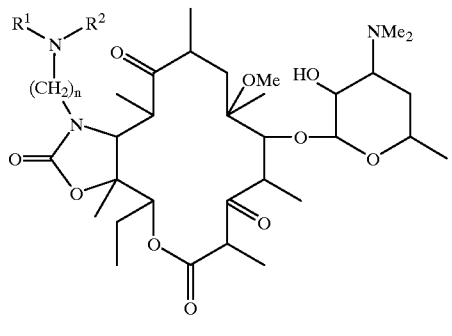

(e)

Step (1); 10,11-Anhydro-2',4"-di-O-acetyl-12-O-imidazolylcarbonyl-6-O-methylerythromycin A described in EP patent No. 638584 is reacted with a diamine such as ethylenediamine or 1,3-diaminopropane in a suitable solvent at a temperature of from −30° C. to 100° C., preferably 0° C. to 30° C. The resulting 11,12-cyclic carbamate compound is reacted in a lower alcohol or an aqueous lower alcohol, if desired, in the presence of a base such as sodium bicarbonate, at a temperature of from 0° C. to 100° C., preferably room temperature to 80° C. to remove the protective group at the 2'-position, thereby there is obtained Compound (a) (wherein n is as defined above). Examples of the suitable solvent to be used herein are acetonitrile, tetrahydrofuran, N,N-dimethylformamide, dioxane, ethyl acetate, N-methylpyrrolidone, an aqueous solution thereof and a mixture thereof. Examples of the lower alcohol to be used herein include methanol, ethanol and propyl alcohol.

Step (2-I); Compound (a) is reacted with quinolylaldehyde, furaldehyde, thiophenecarboxaldehyde, pyridylaldehyde or a substituted benzaldehyde in a slightly excess amount relative to Compound (a) and a reductant in a lower alcohol in the presence of an acid such as acetic acid at a temperature of from −30° C. to 100° C., preferably 0° C. to 60° C. to give Compound (b) (wherein n and $R^1$ are as defined above). The lower alcohol is the same as used in Step (1). Examples of the reductant to be used herein are sodium borohydride, sodium cyanoborohydride and sodium triacetoxyborohydride.

Step (2-II); Compound (b) is reacted using formaldehyde, acetaldehyde, quinolylaldehyde, furaldehyde, thiophenecarboxaldehyde or pyridylaldehyde in the same manner as in Step (2-I) to give Compound (c) (wherein n, $R^1$ and $R^2$ are as defined above).

Step (3); Compound (c) is reacted with an acid to give Compound (d) (wherein n, $R^1$ and $R^2$ are as defined above). Examples of the acid are hydrochloric acid, hydrobromic acid and sulfuric acid, preferably 0.5 to 2 N hydrochloric acid, and if desired, a mixture of the acid with a lower alcohol such as methanol or ethanol.

Step (4); Compound (d) is reacted with acetic anhydride or acetyl halide in an inert solvent to give a compound which is protected with an acetyl group at the 2'-position. Examples of the inert solvent to be used are dichloromethane, dichloroethane and acetone.

Step (5); The compound obtained in Step (4) is oxidized in an inert solvent using chromic acid, chromic acid-pyridine, pyridinium chlorochromate, pyridinium dichromate or an activated dimethyl sulfoxide at a temperature of from −78° C. to 30° C., and then the resulting 3-ketone derivative is oxidized in a lower alcohol or an aqueous lower alcohol, (herein, a base such as sodium bicarbonate may be added), at a temperature of from 0 ° C. to 100° C., preferably room temperature to 30 ° C., followed by removal of the protective group at the 2'-position to give a compound of the present invention represented by Compound (e) (wherein n, $R^1$ and $R^2$ are as defined above). The inert solvent is the same as used in Step (4). Examples of the activating agent of dimethyl sulfoxide are acetic anhydride, trifluoroacetic anhydride, oxalyl chloride, phosphorus pentachloride, pyridinium sulfate, pyridinium trifluoroacetate, 1,3-dicyclohexylcarbodiimide and 1-(3-dimethylaminopropyl)-3-ethylcarbodiimide hydrochloride. The lower alcohol is the same as used in Step (1).

The compounds of the present invention can be administered orally or parenterally in the various preparation forms for the purpose of the application based on the pharmacological properties. The pharmaceutical composition of the present invention can be prepared by homogeneously mixing an effective amount of the compound of the present invention in the free form or in the form of an acid addition salt thereof, with a pharmaceutically acceptable carrier, which may be various forms according to the desired preparation forms. Examples of the preparation forms in the present invention are tablets, capsules, powders, troches, ointments, suspensions, suppositories and injections, all of which can be prepared according to conventional preparation techniques. The dose for treating an adult is from 100 to 1000 mg/day in 2 or 3 divided doses. This dose can be increased or decreased depending on the age, body weight and conditions of the patient.

BEST MODE FOR CARRYING OUT THE INVENTION

The present invention is illustrated in more detail by the following Examples.

EXAMPLE 1

Synthesis of 11-[2-[N,N-bis(3-pyridylmethyl)amino] ethyl]amino-3,11-dideoxy-3-oxo-5-O-desosaminyl-6-O-methylerythronolide A 11,12-cyclic carbamate (1) To a solution of 70.0 g (77 mmol) of 10,11-anhydro-2',4"-di-O-acetyl-12-O-imidazolylcarbonyl-6-O-methylerythromycin A described in European Patent No. 638584 in 1 L of acetonitrile was added 30.0 ml (231 mmol) of ethylenediamine at room temperature, followed by stirring overnight. The reaction solution was evaporated under reduced pressure, and the residue was dissolved in 1 L of methanol and refluxed under heating for 4 hours. After evaporation of the solvent, purification by silica gel column chromatography (chloroform:methanol:aqueous ammonia=20:1:0.1) gave 67.0 g (yield: 97%) of the amine compound.

(2) To a solution of 5.0 g (6.0 mmol) of the compound obtained in the above (1) in 60 ml of methanol were added 2.8 ml (30 mmol) of nicotinaldehyde and 3.9 ml (61 mmol) of acetic acid, followed by addition of 1.9 g (30 mmol) of sodium cyanoborohydride under ice-cooling. The reaction solution was heated to 60° C. and refluxed under heating for 4 hours.

The reaction solution was made basic with 4N sodium hydroxide and extracted with chloroform. The organic layer was dried over anhydrous magnesium sulfate, followed by evaporation of the solvent under reduced pressure. The residue was purified by silica gel column chromatography (chloroform:methanol:aqueous ammonia=20:1:0.1) to give 2.3 g (yield: 38%) of the 11-[2-[N,N-bis(3-pyridylmethyl) amino]ethyl]amino compound.

(3) A solution of 2.3 g of the compound obtained in the above (2) in 30 ml of 1N aqueous hydrochloric acid solution was stirred at room temperature overnight. After the reaction, the mixture was made basic with 4N aqueous sodium hydroxide solution and extracted with chloroform. The organic layer was dried over anhydrous magnesium sulfate, followed by evaporation of the solvent under reduced pressure. The residue was purified by silica gel column chromatography (chloroform:methanol:aqueous ammonia=20:1:0.1) to give 1.7 g (yield: 87%) of the 3-hydroxyl compound.

(4) To a solution of 1.7 g (2.0 mmol) of the compound obtained in the above (3) in 20 ml of methylene chloride was added 0.35 ml (3.1 mmol) of acetic anhydride at room temperature, followed by stirring overnight. The reaction solution was made basic with a saturated aqueous sodium bicarbonate solution and extracted with chloroform. The chloroform layer was washed with distilled water and an aqueous sodium chloride solution. The organic layer was dried over anhydrous magnesium sulfate, followed by evaporation of the solvent under reduced pressure to give 1.7 g (yield: 96%) of the 2'-O-acetyl compound.

(5) To a solution of 0.50 g (0.57 mmol) of the compound obtained in the above (4) in 10 ml of methylene chloride were successively added 0.21 g (1.7 mmol) of 1-(3-dimethylaminopropyl)-3-ethylcarbodiimide hydrochloride, 0.33 g (1.7 mmol) of pyridinium trifluoroacetate and 0.40 ml of dimethyl sulfoxide under ice-cooling, followed by stirring at room temperature overnight. After the reaction, the mixture was washed with distilled water and an aqueous sodium chloride solution, and the organic layer was dried over anhydrous magnesium sulfate, followed by evaporation of the solvent under reduced pressure. The residue was dissolved in 10 ml of methanol and refluxed under heating for 3 hours. After the reaction, the solvent was evaporated, and the residue was purified by silica gel column chromatography (chloroform:methanol:aqueous ammonia=20:1:0.1) to give 0.35 g (yield: 75%) of the title compound.

Mass (FAB; 3-NBA) m/z: 838 $[M+H]^+$

EXAMPLE 2

Synthesis of 11-[2-[N-methyl-N-(3-pyridylmethyl) amino]ethyl]amino-3,11-dideoxy-3-oxo-5-O-desosaminyl-6-O-methylerythronolide A 11,12-cyclic carbamate (1) To a solution of 20.0 g (22.4 mmol) of the compound obtained in Example 1(1) in 200 ml of methanol were added 2.8 ml (29.1 mmol) of nicotinaldehyde and 7.3 ml (112 mmol) of acetic acid, followed by addition of 2.8 g (44.8 mmol) of sodium cyanoborohydride under ice-cooling. The temperature was turned to room temperature, and the mixture was stirred for 4 hours. The reaction solution was made basic with 4N sodium hydroxide and extracted with diethyl ether. The organic layer was dried over anhydrous magnesium sulfate, followed by evaporation of the solvent under reduced pressure. The residue was dissolved in 200 ml of ethanol, and then 30.0 ml (224 mmol) of 37% aqueous formaldehyde solution and 11.0 ml (224 mmol) of 90% aqueous formic acid solution were added thereto. The mixture was refluxed under heating for 3.5 hours, and the reaction solution was concentrated under reduced pressure, made basic with 4N sodium hydroxide and extracted with chloroform. The organic layer was dried over anhydrous magnesium sulfate, and the solvent was evaporated under reduced pressure. The residue was purified by silica gel column chromatography (chloroform:methanol:aqueous ammonia=20:1:0.1) to give 21.0 g (yield: 97%) of the 11-[2-[N-methyl-N-(3-pyridylmethyl)amino]ethyl]amino compound.

(2) Following the same procedure as in Example 1(3) using the compound obtained in the above (1), there was obtained 13.0 g (yield: 82%) of the 3-hydroxyl compound.

(3) Following the same procedure as in Example 1(4) using 13.0 g (17.1 mmol) of the compound obtained in the above (2), there was obtained 12.7 g (yield: 93%) of the 2'-O-acetyl compound.

(4) Following the same procedure as in Example 1(5) using 1.48 g (1.84 mmol) of the compound obtained in the above (3), there was obtained 0.90 g (yield: 62%) of the title compound.

Mass (FAB; 3-NBA) m/z: 761 [M+H]$^+$ $^1$H-NMR (300 MHz, CDCl$_3$) δ (ppm): 0.77 (t, 3H, J=7.25 Hz, H15), 2.17 (s, 3H, NMe), 2.26(s, 6H, NMe$_2$), 2.65 (s, 3H, 6-OMe), 4.23 (d, 1H, J=8.85 Hz, H5), 7.21 (m, 1H), 7.70 (m, 1H), 8.48 (m, 2H).

EXAMPLE 3

Synthesis of 11-[2-[N-methyl-N-(4-quinolylmethyl)amino]ethyl]amino-3,11-dideoxy-3-oxo-5-O-desosaminyl-6-O-methylerythronolide A 11,12-cyclic carbamate (1) Following the same procedure as in Example 2(1) using 1.2 g (7.8 mmol) of 4-quinolinecarboxaldehyde in place of nicotinaldehyde and 5.80 g (6.5 mmol) of the compound obtained in Example 1(1), there was obtained 3.70 g (yield: 56%) of the 11-[2-[N-methyl-N-(4-quinolylmethyl)amino]ethyl]amino compound.

(2) Following the same procedure as in Example 1(3) using 3.60 g (3.5 mmol) of the compound obtained in the above (1), there was obtained 2.40 g (yield: 80%) of the 3-hydroxyl compound.

(3) Following the same procedure as in Example 1(4) using 2.10 g (2.5 mmol) of the compound obtained in the above (2), there was obtained 2.20 g (yield: 99%) of the 2'-O-acetyl compound.

(4) Following the same procedure as in Example 1(5) using 0.70 g (0.82 mmol) of the compound obtained in the above (3), there was obtained 0.36 g (yield: 47%) of the title compound.

Mass (FAB; 3-NBA) m/z: 811 [M+H]$^+$ $^1$H-NMR (300 MHz, CDCl$_3$) δ (ppm): 0.63 (t, 3H, J=7.26 Hz, H15), 2.27 (s, 6H, NMe$_2$), 2.29 (s, 3H, NMe), 2.62 (s, 3H, 6-OMe), 4.22 (d, 1H, J=8.85 Hz, H5).

EXAMPLE 4

Synthesis of 11-[3-[N-methyl-N-(3-pyridylmethyl)amino]propyl]amino-3,11-dideoxy-3-oxo-5-O-desosaminyl-6-O-methylerythronolide A 11,12-cyclic carbamate (1) Following the same procedure as in Example 1(1) using 1,3-diaminopropane in place of ethylenediamine and 14.6 g (16 mmol) of 10,11-anhydro-2',4"-di-O-acetyl-12-O-imidazolylcarbonyl-6-O-methylerythromycin A, there was obtained 10.14 g (yield: 73%) of the 11-(3-aminopropyl)amino compound.

(2) Following the same procedure as in Example 2(1) using 5.8 g (6.7 mmol) of the compound obtained in the above (1), there was obtained the 11-[3-[N-methyl-N-(3-pyridylmethyl)amino]propyl]amino compound, followed by the same procedure as in Example 1(3) to give 2.81 g (yield: 54%) of the 3-hydroxyl compound.

(3) Following the same procedure as in Example 1(4) using 2.30 g (3.0 mmol) of the compound obtained in the above (2), there was obtained 2.22 g of the 2'-O-acetyl compound.

(4) Following the same procedure as in Example 1(5) using 0.87 g (1.06 mmol) of the compound obtained in the above (3), there was obtained 0.64 g (yield: 78%) of the title compound.

Mass (FAB) m/z: 775 [M+H]$^+$

EXAMPLE 5

Synthesis of 11-[3-[N-methyl-N-(2-pyridylmethyl)amino]propyl]amino-3,11-dideoxy-3-oxo-5-O-desosaminyl-6-O-methylerythronolide A 11,12-cyclic carbamate (1) Following the same procedure as in Example 2(1) using 2-pyridinecarboxaldehyde in place of nicotinaldehyde and 4.91 g (5.6 mmol) of the compound obtained in Example 4(1), there was obtained 2.08 g of the 11-[3-[N-methyl-N-(2-pyridylmethyl)amino]propyl]amino compound.

(2) Following the same procedures as in Examples 1(3) and 1(4) using 2.08 g (2.1 mmol) of the compound obtained in the above (1), there was obtained 1.45 g of the 2'-O-acetyl-3-hydroxyl compound.

(3) Following the same procedure as in Example 1(5) using 0.38 g (0.46 mmol) of the compound obtained in the above (2), there was obtained 0.27 g (yield: 74%) of the title compound.

Mass (FAB) m/z: 775 [M+H]$^+$

EXAMPLE 6

Synthesis of 11-[2-[N-methyl-N-(4-nitrobenzyl)amino]ethyl]amino-3,11-dideoxy-3-oxo-5-O-desosaminyl-6-O-methylerythronolide A 11, 12-cyclic carbamate (1) Following the same procedure as in Example 2(1) using 0.61 g (4.0 mmol) of 4-nitrobenzaldehyde in place of nicotinaldehyde and 2.80 g (3.4 mmol) of the compound obtained in Example 1(1), there was obtained the 11-[2-[N-methyl-N-(4-nitrobenzyl)amino]ethyl]amino compound, followed by the same procedure as in Example 1(3) to give 0.90 g (yield: 32%) of the 3-hydroxyl compound.

(2) Following the same procedure as in Example 1(4) using 0.70 g (0.84 mmol) of the compound obtained in the above (1), there was obtained 0.75 g (yield: 100%) of the 2'-O-acetyl compound.

(3) Following the same procedure as in Example 1(5) using 0.27 g (0.31 mmol) of the compound obtained in the above (2), there was obtained 0.15 g (yield: 60%) of the title compound.

Mass (FAB; 3-NBA) m/z: 805 [M+H]$^+$ $^1$H-NMR (300 MHz, CDCl$_3$) δ (ppm): 0.73 (t, 3H, J=7.26 Hz, H15), 2.20 (s, 3H, NMe), 2.27 (s, 6H, NMe$_2$), 2.62 (s, 3H, 6-OMe), 4.22 (d, 1H, J=8.85 Hz, H5), 7.50 (m, 2H), 8.14 (m, 2H).

EXAMPLE 7

Synthesis of 11-[2-[N-methyl-N-(4-methoxybenzyl)amino]ethyl]amino-3,11-dideoxy-3-oxo-5-O-desosaminyl-6-O-methylerythronolide A 11,12-cyclic carbamate (1) Following the same procedure as in Example 2(1) using 0.44 ml (3.6 mmol) of 4-methoxybenzaldehyde in place of nicotinaldehyde and 3.00 g (3.6 mmol) of the compound obtained in Example 1(1), there was obtained the 11-[2-[N-methyl-N-(4-methoxybenzyl)amino]ethyl]amino compound, followed by the same procedure as in Example 1 (3) to give 1.89 g (yield: 61%) of the 3-hydroxyl compound.

(2) Following the same procedure as in Example 1(4) using 1.80 g (2.1 mmol) of the compound obtained in the above (1), there was obtained 1.80 g (yield: 95%) of 2'-O-acetyl compound.

(3) Following the same procedure as in Example 1(5) using 0.50 g (0.55 mmol) of the compound obtained in the above (2), there was obtained 0.35 g (yield: 81%) of the title compound.

Mass (FAB; 3-NBA) m/z: 790 [M+H]$^+$
$^1$H-NMR (200 MHz, CDCl$_3$) δ (ppm): 0.79 (t, 3H, J=7.26 Hz, H15), 2.17 (s, 3H, NMe), 2.26 (s, 6H, NMe$_2$), 2.64 (s, 3H, 6-OMe), 3.79 (s, 3H, Ph-OMe), 4.24 (d, 1H, J=8.57 Hz, H5), 6.81 (m, 2H), 7.22 (m, 2H).

EXAMPLE 8

Synthesis of 11-[2-[(N-methyl-N-furfuryl)amino]ethyl]amino-3,11-dideoxy-3-oxo-5-O-desosaminyl-6-O-methylerythronolide A 11,12-cyclic carbamate (1) Following the same procedure as in Example 2(1) using 0.30 ml (3.6 mmol) of furfural in place of nicotinaldehyde and 3.00 g (3.6 mmol) of the compound obtained in Example 1(1), there was obtained the 11-[2-[(N-methyl-N-furfuryl)amino]ethyl]amino compound, followed by the same procedure as in Example 1(3) to give 1.20 g (yield: 40%) of the 3-hydroxyl compound.

(2) Following the same procedure as in Example 1(4) using 1.10 g (1.3 mmol) of the compound obtained in the above (1), there was obtained 1.0 g (yield: 89%) of the 2'-O-acetyl compound.

(3) Following the same procedure as in Example 1(5) using 0.50 g (0.58 mmol) of the compound obtained in the above (2), there was obtained 0.27 g (yield: 62%) of the title compound.

Mass (FAB; 3-NBA) m/z: 750 [M+H]$^+$
$^1$H-NMR (200 MHz, CDCl$_3$) δ (ppm): 0.84 (t, 3H, J=7.25 Hz, H15), 2.26 (s, 6H, NMe$_2$), 2.29 (s, 3H, NMe), 2.66 (s, 3H, 6-OMe), 4.25 (d, 1H, J=8.79 Hz, H5), 6.16–6.32 (m, 2H), 7.35 (m, 1H).

EXAMPLE 9

Synthesis of 11-[2-[N-methyl-N-(4-pyridylmethyl)amino]ethyl]amino-3,11-dideoxy-3-oxo-5-O-desosaminyl-6-O-methylerythronolide A 11,12-cyclic carbamate (1) Following the same procedure as in Example 2(1) using 0.34 ml (3.6 mmol) of isonicotinaldehyde in place of nicotinaldehyde and 3.00 g (3.6 mmol) of the compound obtained in Example 1(1), there was obtained the 11-[2-[N-methyl-N-(4-pyridylmethyl)amino]ethyl]amino compound, followed by the same procedure as in Example 1(3) to give 1.85 g (yield: 67%) of the 3-hydroxyl compound.

(2) Following the same procedure as in Example 1(4) using 1.60 g (2.1 mmol) of the compound obtained in the above (1), there was obtained 1.56 g (yield: 92%) of the 2'-O-acetyl compound.

(3) Following the same procedure as in Example 1(5) using 0.50 g (0.62 mmol) of the compound obtained in the above (2), there was obtained 0.36 g (yield: 76%) of the title compound.

Mass (FAB; 3-NBA) m/z: 761 [M+H]$^+$
$^1$H-NMR (200 MHz, CDCl$_3$) δ (ppm): 0.72 (t, 3H, J=7.25 Hz, H15), 2.20 (s, 3H, NMe), 2.27 (s, 6H, NMe$_2$), 2.64 (s, 3H, 6-OMe), 4.23 (d, 1H, J=8.79 Hz, H5), 7.28 (m, 2H), 8.50 (m, 2H).

EXAMPLE 10

Synthesis of 11-[2-[N-methyl-N-(2-thienylmethyl)amino]ethyl]amino-3,11-dideoxy-3-oxo-5-O-desosaminyl-6-O-methylerythronolide A 11,12-cyclic carbamate (1) Following the same procedure as in Example 2(1) using 0.34 ml (3.6 mmol) of 2-thiophenealdehyde in place of nicotinaldehyde and 3.00 g (3.6 mmol) of the compound obtained in Example 1(1), there was obtained the 11-[2-[N-methyl-N-(2-thienylmethyl)amino]ethyl]amino compound, followed by the same procedure as in Example 1(3) to give 1.34 g (yield: 46%) of the 3-hydroxyl compound.

(2) Following the same procedure as in Example 1(4) using 1.20 g (1.5 mmol) of the compound obtained in the above (1), there was obtained 1.24 g (yield: 97%) of the 2'-O-acetyl compound.

(3) Following the same procedure as in Example 1(5) using 0.50 g (0.62 mmol) of the compound obtained in the above (2), there was obtained 0.28 g (yield: 59%) of the title compound.

Mass (FAB; 3-NBA) m/z: 766 [M+H]$^+$
$^1$H-NMR (200 MHz, CDCl$_3$) δ (ppm): 0.83 (t, 3H, J=7.25 Hz, H15), 2.27 (s, 6H, NMe$_2$), 2.28 (s, 3H, NMe), 2.66 (s, 3H, 6-OMe), 4.24 (d, 1H, J=8.79 Hz, H5), 6.90 (m, 2H), 7.19 (m, 1H).

EXAMPLE 11

Synthesis of 11-[2-[N-methyl-N-(3,4,5-trimethoxybenzyl)amino]ethyl]amino-3,11-dideoxy-3-oxo-5-O-desosaminyl-6-O-methylerythronolide A 11,12-cyclic carbamate (1) Following the same procedure as in Example 2(1) using 0.71 g (3.6 mmol) of 3,4,5-trimethoxybenzaldehyde in place of nicotinaldehyde and 3.00 g (3.6 mmol) of the compound obtained in Example 1(1), there was obtained the 11-[2-[N-methyl-N-(3,4,5-trimethoxybenzyl)amino]ethyl]amino compound, followed by the same procedure as in Example 1(3) to give 1.99 g (yield: 60%) of the 3-hydroxyl compound.

(2) Following the same procedure as in Example 1(4) using 1.67 g (1.8 mmol) of the compound obtained in the above (1), there was obtained 1.39 g (yield: 80%) of the 2'-O-acetyl compound.

(3) Following the same procedure as in Example 1(5) using 0.50 g (0.52 mmol) of the compound obtained in the above (2), there was obtained 0.30 g (yield: 68%) of the title compound.

Mass (FAB; 3-NBA) m/z: 850 [M+H]$^+$
$^1$H-NMR (200 MHz, CDCl$_3$) δ (ppm): 0.70 (t, 3H, J=7.25 Hz, H15), 2.25 (s, 3H, NMe), 2.26 (s, 6H, NMe$_2$), 2.64 (s, 3H, 6-OMe), 3.83 (s, 3H, Ph-OMe), 3.87 (s, 6H, Ph-OMe), 6.60 (m, 2H).

EXAMPLE 12

Synthesis of 11-[2-[N-methyl-N-(4-dimethylaminobenzyl)amino]ethyl]amino-3,11-dideoxy-3-oxo-5-O-desosaminyl-6-O-methylerythronolide A 11,12-cyclic carbamate (1) Following the same procedure as in Example 2(1) using 0.50 g (3.3 mmol) of 4-dimethylaminobenzaldehyde in place of nicotinaldehyde and 2.50 g (3.0 mmol) of the compound obtained in Example 1(1), there was obtained the 11-[2-[N-methyl-N-(4-dimethylaminobenzyl)amino]ethyl] amino compound, followed by the same procedure as in Example 1(3) to give 2.21 g (yield: 88%) of the 3-hydroxyl compound.

(2) Following the same procedure as in Example 1(4) using 2.00 g (2.4 mmol) of the compound obtained in the above (1), there was obtained 2.00 g (yield: 95%) of the 2'-O-acetyl compound.

(3) Following the same procedure as in Example 1(5) using 0.90 g (1.03 mmol) of the compound obtained in the above (2), there was obtained 0.66 g (yield: 80%) of the title compound.

Mass (FAB; 3-NBA) m/z: 803 [M+H]$^+$ $^1$H-NMR (200 MHz, CDCl$_3$) δ (ppm): 0.81 (t, 3H, J=7.26 Hz, H15), 2.17 (s, 3H, NMe), 2.26 (s, 6H, NMe$_2$), 2.64 (s, 3H, 6-OMe), 2.91 (s, 6H, Ph-NMe$_2$), 6.67 (m, 2H), 7.15 (m, 2H).

EXAMPLE 13

Synthesis of 11-[2-[N-methyl-N-(2-tolylmethyl) amino]ethyl]amino-3,11-dideoxy-3-oxo-5-O-desosaminyl-6-O-methylerythronolide A 11,12-cyclic carbamate (1) Following the same procedure as in Example 2(1) using 0.39 ml (3.3 mmol) of 2-tolualdehyde in place of nicotinaldehyde and 2.50 g (3.0 mmol) of the compound obtained in Example 1(1), there was obtained the 11-[2-[N-methyl-N-(2-tolylmethyl)amino]ethyl]amino compound, followed by the same procedure as in Example 1(3) to give 2.24 g (yield: 96%) of the 3-hydroxyl compound.

(2) Following the same procedure as in Example 1(4) using 2.00 g (2.6 mmol) of the compound obtained in the above (1), there was obtained 1.84 g (yield: 87%) of the 2'-O-acetyl compound.

(3) Following the same procedure as in Example 1(5) using 0.80 g (0.98 mmol) of the compound obtained in the above (2), there was obtained 0.57 g (yield: 75%) of the title compound.

Mass (FAB; 3-NBA) m/z: 774 [M+H]$^+$ $^1$H-NMR (200 MHz, CDCl$_3$) δ (ppm): 0.76 (t, 3H, J=7.26 Hz, H15), 2.18 (s, 3H), 2.26 (s, 6H, NMe$_2$), 2.33 (s, 3H), 2.64 (s, 3H, 6-OMe), 7.10 (m, 3H), 7.30 (m, 1H).

EXAMPLE 14

Synthesis of 11-[2-[N-methyl-N-(3-tolylmethyl) amino]ethyl]amino-3,11-dideoxy-3-oxo-5-O-desosaminyl-6-O-methylerythronolide A 11,12-cyclic carbamate (1) Following the same procedure as in Example 2(1) using 0.39 ml (3.3 mmol) of 3-tolualdehyde in place of nicotinaldehyde and 2.50 g (3.0 mmol) of the compound obtained in Example 1(1), there was obtained the 11-[2-[N-methyl-N-(3-tolylmethyl)amino]ethyl]amino compound, followed by the same procedure as in Example 1(3) to give 1.73 g (yield: 74%) of the 3-hydroxyl compound.

(2) Following the same procedure as in Example 1(4) using 0.80 g (1.0 mmol) of the compound obtained in the above (1), there was obtained 0.78 g (yield: 95%) of the 2'-O-acetyl compound.

(3) Following the same procedure as in Example 1(5) using 0.72 g (0.88 mmol) of the compound obtained in the above (2), there was obtained 0.50 g (yield: 73%) of the title compound.

Mass (FAB; 3-NBA) m/z: 774 [M+H]$^+$ $^1$H-NMR (200 MHz, CDCl$_3$) δ (ppm): 0.78 (t, 3H, J=7.26 Hz, H15), 2.18 (s, 3H), 2.26 (s, 6H, NMe$_2$), 2.32 (s, 3H), 2.64(s, 3H, 6-OMe), 7.00 (m, 1H), 7.12 (m, 3H).

EXAMPLE 15

Synthesis of 11-[2-[N-methyl-N-(2-methoxybenzyl) amino]ethyl]amino-3,11-dideoxy-3-oxo-5-O-desosaminyl-6-O-methylerythronolide A 11,12-cyclic carbamate (1) Following the same procedure as in Example 2(1) using 0.40 ml (3.3 mmol) of 2-methoxybenzaldehyde in place of nicotinaldehyde and 2.50 g (3.0 mmol) of the compound obtained in Example 1(1), there was obtained the 11-[2-[N-methyl-N-(2-methoxybenzyl)amino]ethyl]amino compound, followed by the same procedure as in Example 1(3) to give 2.23 g (yield: 85 %) of the 3-hydroxyl compound.

(2) Following the same procedure as in Example 1(4) using 2.00 g (2.3 mmol) of the compound obtained in the above (1), there was obtained 2.05 g (yield: 98%) of the 2'-O-acetyl compound.

(3) Following the same procedure as in Example 1(5) using 0.50 g (0.64 mmol) of the compound obtained in the above (2), there was obtained 0.35 g (yield: 69%) of the title compound.

Mass (FAB; 3-NBA) m/z: 790 [M+H]$^+$ $^1$H-NMR (200 MHz, CDCl$_3$) δ (ppm): 0.77 (t, 3H, J=7.26 Hz, H15), 2.24 (s, 3H, NMe), 2.26 (s, 6H, NMe$_2$), 2.65 (s, 3H, 6-OMe), 3.80 (s, 3H, Ph-OMe).

EXAMPLE 16

Synthesis of 11-[2-[N-acetyl-N-(3-pyridylmethyl) amino]ethyl]amino-3,11-dideoxy-3-oxo-5-O-desosaminyl-6-O-methylerythronolide A 11,12-cyclic carbamate (1) A solution of 100 g (120 mmol) of the compound obtained in Example 1(1) in 150 ml of 1N aqueous hydrochloric acid solution was stirred at 70° C. for an hour. After the reaction, the reaction mixture was cooled to room temperature and extracted with chloroform. The aqueous layer was made basic with 2N aqueous sodium hydroxide solution, extracted with chloroform and washed with a saturated aqueous sodium chloride solution. The organic layer was dried over anhydrous magnesium sulfate, and the solvent was evaporated under reduced pressure. The resulting residue was recrystallized from ether to give 49 g (yield: 63%) of 11-(2-aminoethyl)amino-11-deoxy-5-O-desosaminyl-6-O-methylerythronolide A 11,12-cyclic carbamate as the first crystals.

(2) To a solution of 100 g (0.15 mol) of the compound obtained in the above (1) in 500 ml of methanol were added 18.4 ml (0.20 mol) of nicotinaldehyde and 15.6 ml (0.28 mol) of acetic acid. After addition of 61.1 g (0.28 mol) of sodium triacetoxyborohydride under ice-cooling, the mixture was stirred at room temperature for 2 days. After the reaction, an aqueous sodium hydroxide solution was added, and the mixture was extracted with chloroform. The organic layer was dried over anhydrous magnesium sulfate, and evaporation of the solvent under reduced pressure gave 131.6 g of 11-[2-[N-(3-pyridylmethyl)amino]ethyl]amino-11-deoxy-5-O-desosaminyl-6-O-methylerythronolide A 11,12-cyclic carbamate.

(3) Following the same procedure as in Example 1(4) using 2.2 g (2.9 mmol) of the compound obtained in the above (2) and 0.83 ml (8.8 mmol) of acetic anhydride, there was obtained 2.47 g of the diacetyl compound.

SIMS m/z: 833 [M+H]$^+$ (4) Following the same procedure as in Example 1(5) using 0.72 g (0.86 mmol) of the compound obtained in the above (3), there was obtained 0.47 g (yield: 69%) of the title compound.

SIMS m/z: 789 [M+H]$^+$ $^1$H-NMR (200 MHz, CDCl$_3$) δ (ppm): 2.27 (s, 6H, NMe$_2$), 3.50 (s, 3H, 6-OMe), 4.21 (d, 1H, J=9.0 Hz, H-5), 4.28 (d, 1H, J=7.0 Hz, H-1'), 4.70 (s, 2H, —NCH$_2$(3-Pyridine)), 4.86 (dd, 1H, J=10.5, 2.2 Hz, H-13)

EXAMPLE 17

Syntheses of 11-[2-[N-(4-quinolylmethyl)amino]ethyl]amino-3,11-dideoxy-3-oxo-5-O-desosaminyl-6-O-methylerythronolide A 11,12-cyclic carbamate and 11-[2-[N,N-bis(4-quinolylmethyl)amino]ethyl]amino-3,11-dideoxy-3-oxo-5-O-desosaminyl-6-O-methylerythronolide A 11,12-cyclic carbamate (1) To a solution of 25.3 g (38.4 mmol) of the compound obtained in Example 16(1) in 300 ml of methylene chloride was added 100 ml of water. 12.9 g (0.15 mol) of sodium bicarbonate and 13.7 ml (0.10 mol) of carbobenzoxy chloride were successively added under ice-cooling, and the mixture was stirred for 8 hours. After the reaction, a saturated aqueous sodium bicarbonate solution was added to the reaction mixture, followed by extraction with chloroform. The organic layer was dried over anhydrous magnesium sulfate, and evaporation of the solvent under reduced pressure gave 38.2 g of the bisbenzyloxycarbonyl compound.

(2) Carrying out oxidation in the same procedure as in Example 1(5) using 34.0 g (0.37 mol) of the compound obtained in the above (1), there was obtained 32.3 g of the 3-ketone compound.

(3) To a solution of 18.4 g (20 mmol) of the compound obtained in the above (2) in 180 ml of methanol were added 5 g of 5% palladium-carbon and 20 ml of acetic acid under a hydrogen atmosphere for catalytic hydrogenation. After the reaction, the catalyst was filtered off through Celite, and the filtrate was evaporated under reduced pressure to give 16.6 g of the amine compound.

(4) To a solution of 1.43 g (2.2 mmol) of the compound obtained in the above (3) in 30 ml of methylene chloride was added 0.34 g (2.2 mmol) of 4-quinolinecarboxaldehyde. After addition of 0.73 g (3.3 mmol) of sodium triacetoxyborohydride under ice-cooling, the mixture was stirred at room temperature for 2 hours. After the reation, an aqueous sodium hydroxide solution was added to the reaction solution, followed by extraction with chloroform. The organic layer was dried over anhydrous magnesium sulfate, the solvent was evaporated under reduced pressure, and the residue was purified by silica gel column chromatography (acetone:n-hexane:triethylamine=10:10:0.2) to give 0.32 g of the mono(4-quinolyl) compound and 0.43 g of the di(4-quinolyl) compound.

Mono(4-quinolyl) Compound

IonSpray MS m/z: 797.4 [M+H]$^+$ $^1$H-NMR (500 MHz, CDCl$_3$) δ (ppm): 2.26 (s, 6H, NMe$_2$), 2.66 (s, 3H, 6-OMe), 3.83 (dd, J=13.4, 6.7 Hz, H-2), 4.21–4.40 (m, 3H, H-1' and —NHCH$_2$(4-quinoline)), 5.22 (dd, 1H, J=11.0, 2.4 Hz, H-13)

$^{13}$C-NMR (125 MHz, CDCl$_3$) δ (ppm): 40.2 (NMe$_2$), 49.2 (—NHCH$_2$(4-quinoline)), 49.9 (6-OMe), 104.0 (C1'), 150.5 (11,12-carbamate), 169.8 (C1), 204.1 (C3), 216.6 (C9)

Bis(4-quinoly) Compound

IonSpray MS m/z: 938.5 [M+H]$^+$ $^1$H-NMR (500 MHz, CDCl$_3$) δ (ppm): 2.26 (s, 6H, NMe$_2$), 2.22 (s, 3H, 6-OMe), 3.79 (dd, J=13.4, 6.7 Hz, H-2), 4.12 (d, 1H, J=9.2 Hz, H-5), 4.24 (d, 1H, J=7.3 Hz, H-1'), 4.30 and 4.5 (each d, each 1H, J$_{gem}$=15.3 Hz, —NCH$_2$(4-quinoline)$_2$), 4.86 (dd, 1H, J=11.0, 2.4 Hz, H-13)

$^{13}$C-NMR (125 MHz, CDCl$_3$) δ (ppm): 40.2 (NMe$_2$), 49.4 (6-OMe), 55.5 (—NCH$_2$(4-quinoline)$_2$), 103.9 (C1'), 157.2 (11,12-carbamate), 169.5 (C1), 203.5 (C3), 216.1 (C9)

EXAMPLE 18

Synthesis of 11-[2-[N-(3-pyridylmethyl)amino]ethyl]amino-3,11-dideoxy-3-oxo-5-O-desosaminyl-6-O-methylerythronolide A 11,12-cyclic carbamate Following the same procedure as in Example 16(2) using 1.61 g (2.4 mmol) of the compound obtained in Example 17(3) and 0.23 ml (2.5 mmol) of nicotinaldehyde, there was obtained 0.19 g (yield: 10%) of the title compound.

SIMS m/z: 747 [M+H]$^+$ $^1$H-NMR (500 MHz, CDCl$_3$) δ (ppm): 2.26 (s, 6H, N(CH$_3$)$_2$), 2.73 (s, 3H, 6-OMe), 4.28 (d, 1H, J=7.3 Hz, H-1'), 5.24 (dd, 1H, J=10.7, 2.4 Hz, H-13)

$^{13}$C-NMR (125 MHz, CDCl$_3$) δ (ppm): 40.2 (N(CH$_3$)$_2$), 49.9 (6-OMe), 50.5 (—NCH$_2$(3-Pyridine)), 103.9 (C1'), 158.0 (11,12-carbamate), 169.6(C1), 203.9 (C3), 216.4 (C9)

EXAMPLE 19

Synthesis of 11-[2-[N-methyl-N-(3-pyridylmethyl)amino]ethyl]amino-3,11-dideoxy-3-oxo-5-O-desosaminyl-6-O-cinnamylerythronolide A 11,12-cyclic carbamate (1) To a solution of 22.9 g (0.022 mol) of 2',4"-O-bis(trimethylsilyl)erythromycin A 9-{O-[1-(1-methylethoxy)cyclohexyl]oxime} described in U.S. Pat. No. 4,990,602 in 230 ml (1:1) of dimethyl sulfoxide—tetrahydrofuran were added 13.1 g of cinnamyl bromide and 2.59 g of potassium hydroxide under ice-cooling, followed by stirring under ice-cooling for 1.5 hours. After the reaction, 5 ml of 50% aqueous dimethylamine solution was added, the mixture was stirred at room temperature for 30 minutes, and water was added thereto, followed by extraction with hexane. The hexane layer was washed with a saturated aqueous sodium chloride solution and drided over anhydrous magnesium sulfate, and the hexane was evaporated. To a solution of the resulting residue in 150 ml of ethanol were added 2.83 ml of 90% formic acid and 150 ml of water at room temperature, and the mixture was refluxed under heating for an hour. After addition of 16.1 g of sodium hydrogensulfite, the mixture was refluxed under heating for 2 hours. The reaction solution was concentrated, and adjusted to pH 11 with 2N aqueous sodium hydroxide solution under ice-cooling. After addition of water, the mixture was extracted with ethyl acetate. The ethyl acetate layer was washed with a saturated aqueous sodium chloride solution and dried over anhydrous magnesium sulfate, and the ethyl acetate was evaporated. The resulting residue was purified by silica gel column chromatography (eluant; chloroform:methanol:aqueous ammonia=94:6:0.6–9:1:0.1) to give 7.76 g of 6-O-cinnamylerythromycin A.

MS (FAB) m/z; 850 [M+H]$^+$ $^1$H-NMR (300 MHz, CDCl$_3$) δ (ppm): 2.29 (s, 6H, N(CH$_3$)$_2$), 3.34 (s, 3H, OCH$_3$), 4.00, 4.20 (each dd, each 1H, J=4.7, 10.9 Hz, OCH$_2$CH=CHPh), 6.32 (ddd, 1H, J=4.7, 10.9, 15.7 Hz, OCH$_2$CH=CHPh), 6.47 (d, 1H, J=15.7 Hz, OCH$_2$CH=CHPh)

(2) Carrying out the same reaction as in Example 1(4) using 5.0 g (5.9 mmol) of the compound obtained in the above (1), there was obtained 5.0 g of the 2'-O-acetyl compound.

MS (FAB) m/z; 892 [M+H]$^+$ (3) To a solution of 2.05 g (2.3 mmol) of the compound obtained in the above (2) in 20 ml of methylene chloride was added 1.8 ml (23 mmol) of pyridine. 0.67 g (2.3 mmol) of triphosgene was added under ice-cooling, and the mixture was stirred for 2 hours. To the reaction solution was added water for decomposition of excess amount of the triphosgene, and the mixture was diluted with chloroform, washed with water and a saturated aqueous sodium chloride solution, and dried over anhydrous magnesium sulfate. After evaporation of the solvent under reduced pressure, the resulting residue was dissolved in 15 ml of N,N-dimethylformamide, and 0.39 g (3.4 mmol) of 1,1,3,3-tetramethylguanidine was added thereto, followed by stirring at 100° C. for 3 hours. After allowing to stand for cooling, the mixture was diluted with ethyl acetate, and separated with water. The organic layer was successively washed with water and a saturated aqueous sodium chloride solution, and drided over anhydrous magnesium sulfate. Evaporation of the solvent under reduced pressure gave 1.9 g of 2'-O-acetyl-10,11-anhydro-6-O-cinnamylerythromycin A.

(4) To a solution of 1.9 g (2.2 mmol) of the compound obtained in the above (3) in 20 ml of 1,2-dichloroethane were added 4.1 g (26 mmol) of 1,1'-carbonyldiimidazole and 1.6 g (12 mmol) of 4-dimethylaminopyridine, and the mixture was refluxed under heating for an hour. After allowing to stand for cooling, the reaction solution was diluted with chloroform and separated with a saturated aqueous ammonium chloride solution, and the organic layer was successively washed with water and a saturated aqueous sodium chloride solution, and dried over anhydrous magnesium sulfate. After evaporation of the solvent under reduced pressure, the residue was purified by silica gel column chromatography to give 1.3 g of the 12-O-imidazolylcarbonyl compound.

(5) Carrying out the same reactions as in Examples 1(1), 2(1), 2(2), 2(3) and 2(4) using 1.2 g (1.24 mmol) of the compound obtained in the above (4), there was obtained 0.55 g of the title compound.

MS (FAB) m/z; 863 [M+H]$^+$ $^1$H-NMR (300 MHz, CDCl$_3$) δ (ppm): 2.02 (s, 3H, NCH$_3$), 2.26 (s, 6H, N(CH$_3$)$_2$).

Experiment [In Vitro Antibacterial Activity]

The in vitro antibacterial activity of the compound obtained in Example 2 as an example of the compound of the present invention against various experimental bacteria was measured using sensitive disc media (produced by Eiken Chemical Co.) according to the MIC measuring method specified by the Japan Society of Chemotherapy. Clarithromycin was used as a comparative drug. The results are expressed as MIC value (Minimum Inhibitory Concentration, μg/ml), and shown in Table 1. The compound obtained in Example 2 shows to have a strong antibacterial activity not only against erythromycin-sensitive bacteria but also erythromycin-resistant bacteria and Haemophilus influenzae.

TABLE 1

| In Vitro Antibacterial Activity: MIC (μg/ml) | | |
|---|---|---|
| Compound Microorganism | Compound of Example 2 | Comparative drug |
| S. aureus 209P-JC | 0.05 | 0.10 |
| S. aureus Smith | 0.10 | 0.20 |
| S. epidermidis IID 866 | 0.10 | 0.20 |
| E. faecalis CSJ 1212 | 0.05 | 0.20 |
| S. pneumoniae BM 225 | 0.39 | 50 |
| S. pneumoniae BM 211 | 50 | >100 |

Industrial Applicability

The compounds of the present invention have a strong antibacterial activity against not only erythromycin-sensitive bacteria but also erythromycin-resistant bacteria and Haemophilus influenzae. Therefore, the compounds of the present invention are useful as antibacterial agents for the treatment of bacterially infectious diseases in human beings and animals (including farm animals).

What is claimed is:

1. A pharmaceutical composition comprising an effective amount of an erythromycin A derivative represented by the following formula:

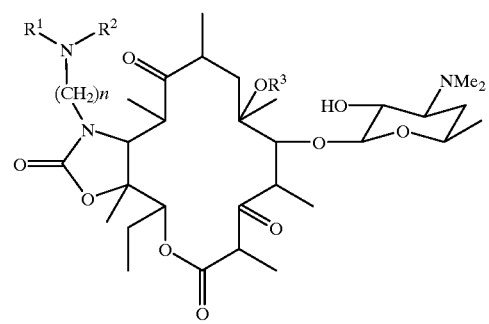

wherein n is an integer of 2 to 4, R$^1$ is a pyridylmethyl group, a furylmethyl group, a thienylmethyl group or a quinolylmethyl group, R$^2$ is the same group as defined for R$^1$, a hydrogen atom, an alkyl group having 1 to 5 carbon atoms, an acetyl group or a pyridylacetyl group, and R$^3$ is an alkyl group having 1 to 5 carbon atoms or a cinnamyl group, or a pharmaceutically acceptable salt thereof, and a pharmaceutically acceptable carrier.

2. A method for the treatment of a bacterially infectious disease which comprises administering a pharmaceutically effective amount of the pharmaceutical composition according to claim 1 to a patient in need of the treatment.

* * * * *